United States Patent [19]
Yano et al.

[11] Patent Number: 5,833,813
[45] Date of Patent: Nov. 10, 1998

[54] METHOD OF RECOVERING AND DEHYDRATING ETHYLENE SULFIDE

[75] Inventors: Hitoshi Yano; Yoshinari Yamaguchi, both of Suita; Hirokazu Ito, Kobe; Ryuichi Ishikawa, Sakai; Yukihiro Matsumoto, Kobe; Teruhisa Kaziwara, Himeji, all of Japan

[73] Assignee: Nippon Shokubai Co., Ltd., Osaka, Japan

[21] Appl. No.: 737,207

[22] PCT Filed: Apr. 2, 1996

[86] PCT No.: PCT/JP96/00890
§ 371 Date: Nov. 7, 1996
§ 102(e) Date: Nov. 7, 1996

[87] PCT Pub. No.: WO96/31495
PCT Pub. Date: Oct. 10, 1996

[30] Foreign Application Priority Data

Apr. 5, 1994 [JP] Japan ................................ 7-080396
Apr. 11, 1995 [JP] Japan ................................ 7-085637

[51] Int. Cl.[6] .................................................. B01D 3/00
[52] U.S. Cl. .................................................. 203/73
[58] Field of Search .................................................. 203/73

[56] References Cited

U.S. PATENT DOCUMENTS

| | | | |
|---|---|---|---|
| 3,622,597 | 11/1971 | Fletcher et al. | 260/327 |
| 3,687,976 | 8/1972 | Wright | 260/327 |
| 3,822,288 | 7/1974 | Labat | 260/327 |
| 3,857,759 | 12/1974 | Fiore et al. | 203/29 |
| 5,304,656 | 4/1994 | Yano et al. | 549/1 |

FOREIGN PATENT DOCUMENTS

| | | |
|---|---|---|
| 49-62469 A | 6/1974 | Japan . |
| 51-23503 B1 | 7/1976 | Japan . |
| 5-339257 A | 12/1993 | Japan . |
| 7-70079 A | 3/1995 | Japan . |
| 6 512 117 | 3/1966 | Netherlands . |
| 7 001 172 | 6/1970 | Netherlands . |
| 1135800 | 12/1968 | United Kingdom . |

OTHER PUBLICATIONS

A.D.B. Sloan, "Cyclodehydration of 2–Mercaptoalkanois as a Route to Episulphides", J. Chem. Soc. (C) 1969, pp. 1252–1256.

Primary Examiner—Edward J. Cain
Attorney, Agent, or Firm—Kubovcik & Kubovcik

[57] ABSTRACT

A method of recovering ethylene sulfide from a hydrous stock solution (solution) containing ethylene sulfide, toluene (hydrophobic organic compound) having a higher boiling point than ethylene sulfide, and a compound having a higher boiling point than toluene, by distilling the stock solution continuously using a continuous fractionating tower 2, a fractionating tower 4, and a rectifying tower 5. Ethylene sulfide is distilled out with toluene and water from the continuous fractionating tower 2, and the distillate is allowed to separate into an oil layer and a water layer in a separating tank 3. The oil layer is distilled continuously by the fractionating tower 4 without being subjected to a reflux operation to distill out water with a part of ethylene sulfide. The bottom product from the fractionating tower 4 is rectified by the rectifying tower 5 to recover ethylene sulfide. Consequently, the polymerization reaction of ethylene sulfide can be suppressed and ethylene sulfide can be separated and recovered continuously in an efficient and stable manner. Also, the clogging of fractionating towers and pipes can be prevented.

33 Claims, 5 Drawing Sheets

METHOD OF RECOVERING AND DEHYDRATING ETHYLENE SULFIDE

FIELD OF THE INVENTION

The present invention relates to a method of recovering ethylene sulfide. The present invention also relates to a method of dehydrating hydrous ethylene sulfide while suppressing polymerization of the same. Ethylene sulfide is highly reactive, and therefore, known as an advantageous compound for use as a raw material of medical supplies, agricultural chemicals, industrial chemicals, sulfur-containing polymers, etc.

BACKGROUND OF THE INVENTION

Ethylene sulfide is an oil compound having a specific gravity of approximately 1 and a boiling point of 55° C. According to the prior art references and the best knowledge of the inventors of the present invention, ethylene sulfide is, in brief, characterized in that:

① it does not mix with water;
② it forms an azeotrope with water at about 51° C. under normal pressure in the azeotropic composition ratio to water 95:5 in weight;
③ when it is in the form of liquid, it becomes unstable upon direct contact with water and eventually turns into a polymer, or a white solid material having a higher melting point; and
④ it reacts with mercaptans quickly to form a ring-opening addition product.

Conventional example methods of synthesizing ethylene sulfide are set forth in U.S. Pat. Nos. 3,687,976 and 3,622,597, U.K. Patent No. 1,135,800, Dutch Patent Nos. 7,001,172 and 6,512,117, J. Chem. Soc. (Sect C) 1252 (1969), etc. In addition, a method subjecting 2-mercaptoethanol to contact dehydration (intramolecular dehydration) in a gaseous phase is proposed to produce ethylene sulfide for industrial use, and a useful catalyst for such a dehydration reaction is disclosed in Japanese Laid-Open Patent Application No. 202027/1993 (Tokukaihei 5-202027). Also, Japanese Laid-Open Patent Application No. 339257/1993 (Tokukaihei 5-339257) discloses a method of scavenging ethylene sulfide obtained as a result of the above dehydration reaction using a hydrophobic organic compound.

According to the above scavenging method, ethylene sulfide is scavenged in the form of a solution of the hydrophobic organic compound with 2-mercaptoethanol as a non-reacted raw material, sulfide compounds as a by-product, and a small quantity of water.

Ethylene sulfide is preserved in the form of a solution of the hydrophobic organic compound in co-existence with a known stabilizer, such as alkylmercaptan and thioamide compounds, and a small quantity of water. In general, a compound having a higher boiling point than ethylene sulfide is used as the hydrophobic organic compound because of its industrial advantages, such as readiness in handling.

The aforementioned prior art references disclose the method of producing ethylene sulfide. However, all the references remain silent about a method of isolating ethylene sulfide from a resulting reactant mixture and purifying the same in a stable manner. In short, no reference discloses a method of recovering ethylene sulfide. Besides, a method of producing ethylene sulfide for industrial use has not been fully established.

As previously mentioned, the hydrophobic organic compound has a higher boiling point than ethylene sulfide which is actually an oil product. Thus, to separate and recover ethylene sulfide from a solution of the hydrophobic organic compound, the solution of the hydrophobic organic compound is distilled continuously using a fractionating tower, so that ethylene sulfide and water form an azeotrope having the lowest boiling point in the distillation system. In other words, since ethylene sulfide and water form an azeotrope, water dissolved and/or suspended in the solution of the hydrophobic organic compound is distilled out with ethylene sulfide from the fractionating tower.

However, when the resulting distillate is cooled, ethylene sulfide in the form of liquid touches water, and eventually turns into a polymer having a high melting point. Thus, some of ethylene sulfide is lost as it undergoes the polymerization, thereby reducing a recovering percentage of ethylene sulfide. Moreover, the fractionating tower or pipes clog with deposits of the resulting polymer, which makes continuous distillation difficult.

Thus, there has been an increasing need to a method of separating and recovering ethylene sulfide from a hydrous solution containing ethylene sulfide, a hydrophobic organic compound, and a compound having a high boiling point, such as a sulfide compound, without causing any of the aforementioned problems. The present invention therefore has a first object to provide a new recovering method which can separate and recover ethylene sulfide in an efficient and stable manner from a hydrous solution containing ethylene sulfide, a hydrophobic organic compound, and a compound having a high boiling point by continuously distilling the solution.

Further, as previously mentioned, ethylene sulfide in the form of liquid starts to polymerize when brought into contact with water and eventually turns into a white polymer. However, a method which can dehydrate hydrous ethylene sulfide while suppressing the polymerization of the same has not been known yet.

In other words, the above prior art references are silent about the method of dehydrating hydrous ethylene sulfide while suppressing the polymerization of the same. For example, while hydrous ethylene sulfide is continuously distilled by the fractionating tower to obtain dehydrated (dry) ethylene sulfide, ethylene sulfide and water form an azeotrope. Thus, ethylene sulfide starts to polymerize in the fractionating tower or pipes and eventually turns into a polymer having a high melting point as previously mentioned. That is to say, the fractionating tower or pipes clog with deposits of the resulting polymer, which makes continuous distillation difficult. Besides, some of ethylene sulfide is lost as a result of the polymer production.

Ethylene sulfide may be dehydrated using available dehydrating agents. However, as previously mentioned, ethylene sulfide is highly reactive, and readily starts the polymerization reaction, side-reaction or the like when brought into contact with the dehydrating agents. Further, there remains an after-treatment problem, such as disposal of the used dehydrating agents with the deposits of toxic ethylene sulfide. Thus, using the available dehydrating agents causes various problems that make the dehydrating method almost infeasible for industrial use.

Accordingly, there has been an increasing need to a method of dehydrating hydrous ethylene sulfide. The present invention therefore has a second object to provide a new method of dehydrating hydrous ethylene sulfide efficiently while suppressing the polymerization of the same to obtain dry ethylene sulfide in a stable manner.

DISCLOSURE OF THE INVENTION

The inventors of the present invention continued the study to provide a new method of recovering ethylene sulfide, and discovered that the polymerization reaction of ethylene sulfide can be suppressed by distilling out a hydrophobic organic compound together with ethylene sulfide and water during the process of continuously distilling a solution of the hydrophobic organic compound using a fractionating tower, thereby making it possible to separate and recover ethylene sulfide efficiently in a stable manner.

More specifically, to solve the above problems, the method of recovering ethylene sulfide of the present invention continuously distills a hydrous solution containing ethylene sulfide, a hydrophobic organic compound having a higher boiling point than ethylene sulfide, and a compound having a higher boiling point than the hydrophobic organic compound using a first fractionating tower, and characteristically distills out ethylene sulfide with the hydrophobic organic compound and water during the above continuous distilling process.

The inventors of the present invention continued the study to also provide a new method of dehydrating ethylene sulfide, and discovered that hydrous ethylene sulfide can be dehydrated efficiently while suppressing the polymerization reaction of the same by letting a hydrophobic organic compound having a higher boiling point than ethylene sulfide co-exist with hydrous ethylene sulfide, so that water is distilled out with a part of ethylene sulfide, while a mixture of ethylene sulfide and the hydrophobic organic compound is released from the bottom during the process of continuously distilling hydrous ethylene sulfide using a fractionating tower, thereby making it possible to obtain dry ethylene sulfide in a stable manner.

That is to say, to solve the above problems, the method of dehydrating ethylene sulfide of the present invention is characterized in that hydrous ethylene sulfide and the hydrophobic organic compound having a higher boiling point than ethylene sulfide are steadily supplied to the fractionating tower and continuously distilled to distill out water with a part of ethylene sulfide, while releasing a mixture of ethylene sulfide and the hydrophobic organic compound from the bottom.

For a fuller understanding of the nature and advantages of the invention, reference should be made to the ensuing detailed description taken in conjunction with the accompanying drawings.

DESCRIPTION OF THE PREFERRED EMBODIMENTS

Figure 1:
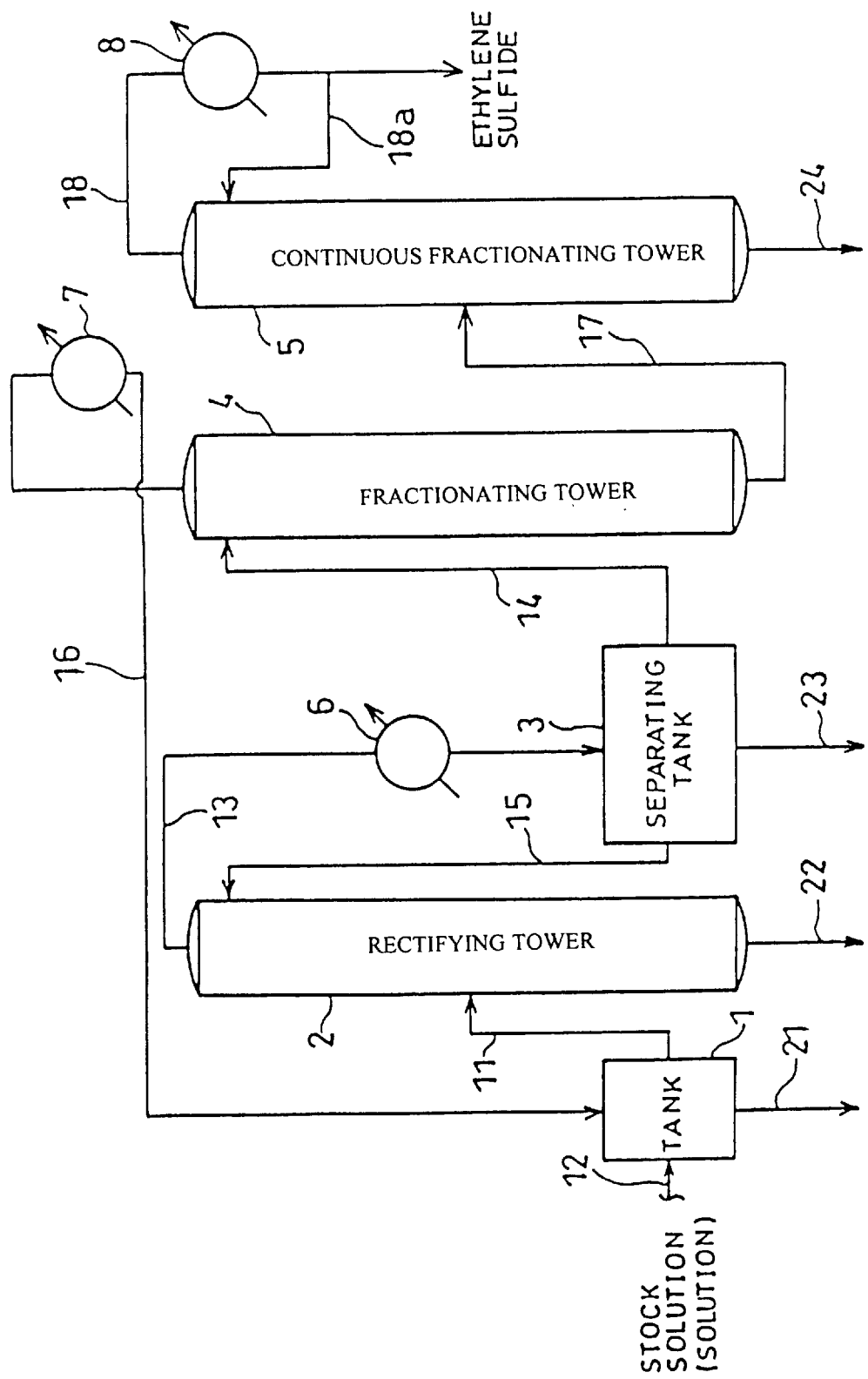
FIG. 1 is a block diagram showing a schematic structure of a distillation apparatus suitably used for a method of recovering ethylene sulfide in accordance with an example embodiment of the present invention.

The following description will describe the present invention in detail.

To begin with, a method of recovering ethylene sulfide will be explained.

In the method of recovering ethylene sulfide of the present invention, a solution used as a stock solution, subject to distillation operation, is a hydrous mixed solution of ethylene sulfide, a hydrophobic organic compound having a higher boiling point than ethylene sulfide, a compound having a higher boiling point than the hydrophobic organic compound. The above solution can be readily produced by any conventional method of producing ethylene sulfide. Examples of such a solution include, but are not limited to: a scavenge liquid made by scavenging ethylene sulfide obtained through contact dehydration of 2-mercaptoethanol in a gaseous phase using the hydrophobic organic compound (Japanese Laid-Open Patent Application No. 339257/1993 (Tokukaihei 5-339257); a preserved solution of ethylene sulfide in the form of a solution of a hydrophobic organic compound in co-existance with a known stabilizing agent, such as alkylmercaptan and thioamide compound; etc.

Examples of the compound having a high boiling point include, but are not limited to: 2-mercaptoethanol as a non-reacted raw material, a sulfide compound as a by-product, and a sulfur-containing compound, such as mercaptanes; impurities; etc.

The above hydrophobic organic compound is not especially limited, and any compound which has a higher boiling point than ethylene sulfide and remains inactive to ethylene sulfide and the compound having a high boiling point can be used as the hydrophobic organic compound. Examples of the hydrophobic organic compound include:

aromatic hydrocarbons, such as benzene, toluene, xylene, pseudocumene, diethylbenzene, and tetralin;

halogen-containing aromatic compounds, such as fluorobenzene, hexafluorobenzene, chlorobenzene, and chlorotoluene;

aliphatic hydrocarbons, such as hexane, decane, isooctane, cyclohexane, and methylcyclohexane;

halogen-containing aliphatic compounds, such as chloroform, carbon tetrachloride, 1,2-dichloroethane, and fluorocyclohexane;

ether compounds, such as dipropyl ether, butylmethyl ether, and phenylmethyl ether;

ketone compounds, such as 3-hexanone, 2-heptanone, cyclohexanone, and phenylmethylketone;

ester compounds, such as phenyl acetate, and methyl benzoate; etc.

Of all these example compounds, the aromatic hydrocarbons and aliphatic hydrocarbons are preferred because of their industrial advantages, such as readiness in handling, and the hydrocarbons having more than five carbon atoms with a relatively large difference in boiling point from ethylene sulfide are particularly preferable because they are readily distilled (rectified).

A method of recovering ethylene sulfide continuously from the above solution will be explained in the following. In the first place, an example distillation apparatus suitably used for recovering ethylene sulfide will be explained with reference to FIG. 1. Note that the structure of the distillation apparatus is not limited to the one shown in FIG. 1.

As shown in FIG. 1, the distillation apparatus comprises a tank 1, a continuous fractionating tower (first fractionating tower) 2, a separating tank 3, a fractionating tower (second fractionating tower) 4, a rectifying tower (third fractionating tower) 5, and three condensers 6 through 8.

The tank 1 constantly reserves a predetermined quantity of the above solution (stock solution). The tank 1 is connected to the three following portions: (1) the middle stage portion of the continuous fractionating tower 2 through a pipe 11; (2) an unillustrated ethylene sulfide producing apparatus or stock solution supply tank through a pipe 12; and (3) the overhead portion of the fractionating tower 4 through a pipe 16 and the condenser 7. A pipe 21 is provided to the tank 1 at the bottom to release water separated from the solution as occasion demands. The middle stage portion referred herein means all the intermediate stages between the top and bottom stages of the fractionating tower.

The stock solution is supplied steadily to the tank 1 from the ethylene sulfide producing apparatus or stock solution supply tank, while the distillate from the fractionating tower 4 is steadily returned to the tank 1. On the other hand, the tank 1 steadily supplies the solution to the middle stage portion of the continuous fractionating tower 2.

The continuous fractionating tower 2 is a so-called diffusing tower for diffusing ethylene sulfide, and it distills the solution continuously. The middle stage portion of the continuous fractionating tower 2 is connected to the tank 1 through the pipe 11, and the overhead portion of the same is connected to the separating tank 3 through a pipe 13 and condenser 6. A pipe 22 is provided to the continuous fractionating tower 2 at the bottom portion to release the bottom product therein. Further, a pipe 15 is provided to the continuous fractionating tower 2 in the vicinity of its overhead portion.

The solution is supplied steadily to the middle stage portion of the continuous fractionating tower 2 from the tank 1. On the other hand, the continuous fractionating tower 2 distills out ethylene sulfide with a hydrophobic organic compound and water as distillate, while releasing the hydrophobic organic compound including a compound having a high boiling point as the bottom product. A part of an oil layer (which will be described below) is returned to the continuous fractionating tower 2 in the vicinity of its overhead portion from the separating tank 3.

The condenser 6 is provided to a predetermined position of the pipe 13 to condense and liquefy a gas (distillate) distilled out from the continuous fractionating tower 2.

The separating tank 3 is a so-called decanter allowing the distillate from the continuous fractionating tower 2 to stand, so that the distillate separates into an oil layer and a water layer. The separating tank 3 is connected to the overhead portion of the continuous fractionating tower 2 through the pipe 13 and condenser 6. Two pipes 14 and 15 are provided to the separating tank 3 at adequate positions to release the oil layer from the separating tank 3. The pipe 14 is connected to the fractionating tower 4 in the vicinity of its overhead portion while the pipe 15 is connected the continuous fractionating tower 2 in the vicinity of its overhead portion. Further, a pipe 23 is provided to the separating tank 3 at the bottom to release the water layer from the separating tank 3.

The distillate from the continuous fractionating tower 2 is supplied steadily to the separating tank 3. On the other hand, the separating tank 3 steadily supplies the oil layer to the fractionating tower 4 in the vicinity of its overhead portion while steadily returning a part of the oil layer to the continuous fractionating tower 2 in the vicinity of its overhead portion. The water layer is released from the bottom of the separating tank 3 as occasion demands. Note that the above oil layer contains a minute quantity of water.

The fractionating tower 4 does not carry out a reflux operation, in other words, it sets the reflux ratio to zero in practice and distills the oil layer continuously to dehydrate the oil layer completely. The overhead portion of the fractionating tower 4 is connected to the tank 1 through the pipe 16 and condenser 7, while the bottom portion of the same is connected to the middle stage portion of the rectifying tower 5 through a pipe 17. Further, the pipe 14 is provided to the fractionating tower 4 in the vicinity of its overhead portion.

The oil layer is supplied steadily to the fractionating tower 4 in the vicinity of its overhead portion from the separating tank 3. On the other hand, the fractionating tower 4 distills out water with a part of ethylene sulfide as distillate, while releasing a mixture of ethylene sulfide and the hydrophobic organic compound as the bottom product.

The condenser 7 is provided to a predetermined position of the pipe 16 to condense and liquefy a gas (distillate) distilled out from the fractionating tower 4.

The rectifying tower 5 rectifies the above mixture to separate and recover, namely, purify, ethylene sulfide. The middle stage portion of the rectifying tower 5 is connected to the bottom portion of the fractionating tower 4 through the pipe 17. The overhead portion of the rectifying tower 5 is connected to an unillustrated ethylene sulfide reservoir tank through a pipe 18 and the condenser 8. Further, the bottom portion of the rectifying tower 5 is connected to an unillustrated hydrophobic organic compound recovering apparatus through a pipe 24. Also, a pipe 18a branched from the pipe 18 is provided to the rectifying tower 5 in the vicinity of its overhead portion.

The above mixture is steadily supplied to the middle stage portion of the rectifying tower 5 from the bottom portion of the fractionating tower 4. On the other hand, the rectifying tower 5 distills out ethylene sulfide as distillate while releasing the hydrophobic organic compound as the bottom product. A part of ethylene sulfide is returned to the rectifying tower 5 in the vicinity of its overhead portion.

The condenser 8 is provided to a predetermined position of the pipe 18 to condense a gas (distillate) distilled out from the rectifying tower 5 to produce a liquid of ethylene sulfide.

Although it is not illustrated in the drawing, the distillation apparatus further comprises components necessary for the distillation operation other than the aforementioned components, such as a heat exchanger, a pump, and an intermediate tank.

Next, an example method of recovering ethylene sulfide using the above-structured distillation apparatus will be explained.

To begin with, the solution used as the stock solution is steadily supplied to the tank 1, while at the same time, the solution is steadily supplied to the middle stage portion of the continuous fractionating tower 2 from the tank 1. The solution supplied to the continuous fractionating tower 2 is distilled continuously, so that ethylene sulfide, water and a part of the hydrophobic organic compound are distilled out from the overhead of the continuous fractionating tower 2 as distillate. On the other hand, the compound having a high boiling point and the rest of the hydrophobic organic compound are released from the bottom as the bottom product. Although ethylene sulfide reacts moderately with mercaptans, one of the compounds having a high boiling point, to produce a ring-opening addition product, ethylene sulfide is separated from mercaptans quickly during the distillation by the continuous fractionating tower 2, thereby reducing the loss amount due to such addition reaction.

The composition of the distillate, that is, a composition ratio of the aforementioned three elements is determined by the distillation conditions in the continuous fractionating tower 2, such as the temperatures at the overhead and bottom, the number of stages in the tower, and the quantity of the oil layer returned from the separating tank 3. In other words, changing the distillation conditions in the continuous fractionating tower 2 can change the composition of the distillate and bottom product of the continuous fractionating tower 2. The distillation by the continuous fractionating tower 2 is carried out under either normal or reduced pressure. Note that it is not azeotropic distillation but by so-called "association", through which the hydrophobic organic compound is distilled out with ethylene sulfide and water.

A preferred quantity of ethylene sulfide in the distillate is 75 percent by weight or less. Containing ethylene sulfide more than 75 percent by weight is not preferable for the following reasons. Since ethylene sulfide has a specific gravity of about 1, if the distillate contains a large quantity of water, there will be only a small difference in specific gravity between the oil and water layers. Then, the oil-water separation in the separating tank 3 ends unsatisfactory, more precisely, even when the distillate is allowed to stand, the distillate does not separate into the oil and water layers. Moreover, such unsatisfactory oil-water separation causes a liquid of ethylene sulfide to touch water with increasing frequency. Therefore, the polymerization reaction of ethylene sulfide, namely, the production of a polymer, is undesirably accelerated. Further, a large quantity of water is supplied to the fractionating tower 4 when the oil-water separation is unsatisfactory. Then, not only ethylene sulfide contained in the distillate from the fractionating tower 4 increases in quantity, but also the production of a polymer of ethylene sulfide in the fractionating tower 4 is accelerated undesireably.

Next, the distillate from the continuous fractionating tower 2 is steadily supplied to the separating tank 3. The distillate is allowed to stand in the separating tank 3 to separate into the oil and water layers. Then, the oil layer is steadily supplied to the fractionating tower 4 in the vicinity of its overhead portion, while the water layer is released from the bottom of the separating tank 3. Also, a part of the oil layer is steadily returned to the continuous fractionating tower 2 in the vicinity of its overhead portion.

Since a part of the oil layer is returned from the separating tank 3 to the continuous fractionating tower 2, the continuous fractionating tower 2 can obtain the similar effects to those obtained when it carries out a typical reflux operation. Thus, the distillate from the continuous fractionating tower 2 is completely free of the compound having a high boiling point. Also, of the oil and water layers contained in the distillate, the oil layer alone is returned to the continuous fractionating tower 2. Thus, no water is returned to the continuous fractionating tower 2 in practice, and therefore, the polymerization reaction of ethylene sulfide, namely, the production of a polymer, can be suppressed in the continuous fractionating tower 2.

Next, the oil layer is steadily supplied from the separating tank 3 to the fractionating tower 4 in the vicinity of its overhead portion. The oil layer supplied to the fractionating tower 4 is distilled continuously, so that a part of ethylene sulfide and water are distilled out from the overhead as distillate. The rest (substantial part) of ethylene sulfide and the hydrophobic organic compound are released from the bottom of the fractionating tower 4 as the bottom product. The fractionating tower 4 continuously distills the oil layer supplied to the same in the vicinity of its overhead portion by setting the reflux ratio to zero in practice to dehydrate the oil layer quickly and completely. As a result, the time water remains in the fractionating tower 4 can be reduced, thereby suppressing the polymerization reaction of ethylene sulfide, namely, the production of a polymer, in the fractionating tower 4.

The composition of the distillate from the fractionating tower 4, that is, a composition ratio of the aforementioned two elements is determined by the distillation conditions in the fractionating tower 4, such as the temperatures at the overhead and bottom, and the number of stages in the tower. In other words, changing the distillation conditions in the fractionating tower 4 can change the composition of the distillate and bottom product of the fractionating tower 4. The distillation by the fractionating tower 4 can be carried out under either normal or reduced pressure. Note that the distillate from the fractionating tower 4 hardly contains hydrophobic organic compound. The weight ratio of ethylene sulfide to water in the distillate from the fractionating tower 4 and the weight ratio of ethylene sulfide to water in the distillate from the continuous fractionating tower 2 are different.

The distillate from the fractionating tower 4 is steadily returned to the tank 1, so that the composition of the solution in the tank 1 does not vary. In other words, the composition of the solution supplied to the continuous fractionating tower 2 can be maintained at a specific ratio. Thus, the distillation system becomes stable and the distillation operation can be carried out in a stable manner. Also, since it has become possible to supply ethylene sulfide contained in the distillate from the fractionating tower 4 to the continuous fractionating tower 2 again, the recovery percentage of ethylene sulfide can be further improved. Subsequently, the bottom product from the fractionating tower 4 is steadily supplied to the middle stage portion of the rectifying tower 5. The bottom product supplied to the rectifying tower 5 is rectified continuously to distill out ethylene sulfide from the overhead as distillate and release the hydrophobic organic compound from the bottom as the bottom product. The rectifying tower 5 carries out a typical rectifying operation. Note that the distillation conditions, such as temperatures at the overhead and bottom, the number of stages in the tower, and reflux ratio, are not especially limited.

Ethylene sulfide is continuously recovered from the solution by the above distillation operation. The hydrophobic organic compound can be readily recovered by, for example, distilling the bottom product from the rectifying tower 5 using a hydrophobic organic compound recovering apparatus. The recovered hydrophobic organic compound is recycled, for example, returned to the ethylene sulfide producing apparatus.

Figure 2:
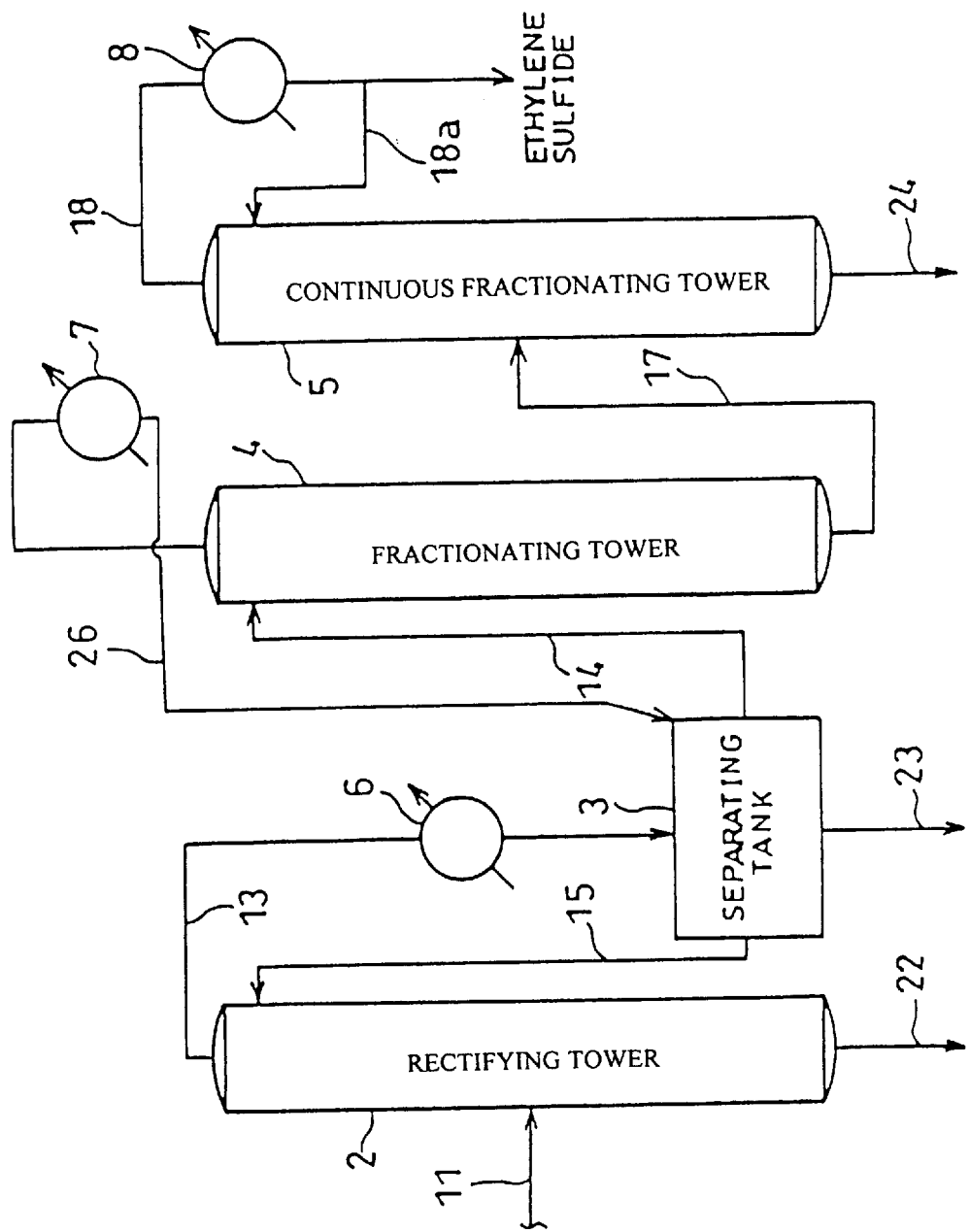
FIG. 2 is a block diagram showing a schematic structure of a distillation apparatus suitably used for a method of recovering ethylene sulfide in accordance with another example embodiment of the present invention.

The structure of the distillation apparatus used for recovering ethylene sulfide is not limited to the structure of FIG. 1, and the distillation apparatus can be of other structures. For example, as shown in FIG. 2, the pipe 16 (FIG. 1) connecting the overhead portion of the fractionating tower 4 to the tank 1 may be replaced with a pipe 26 which connects the overhead portion of the fractionating tower 4 to the separating tank 3.

When the distillation apparatus adopts the above structure, the distillate from the fractionating tower 4 is steadily returned to the separating tank 3, so that the composition of the oil layer in the separating tank 3 does not vary. In other words, the composition of the oil layer supplied to the fractionating tower 4 can be maintained at a specific ratio. Thus, the distillation system becomes stable, and the distillation operation can be carried out in a stable manner. Since ethylene sulfide contained in the distillate from the fractionating tower 4 is supplied to the fractionating tower 4 again, the recovery percentage of ethylene sulfide can be further improved.

Figure 3:
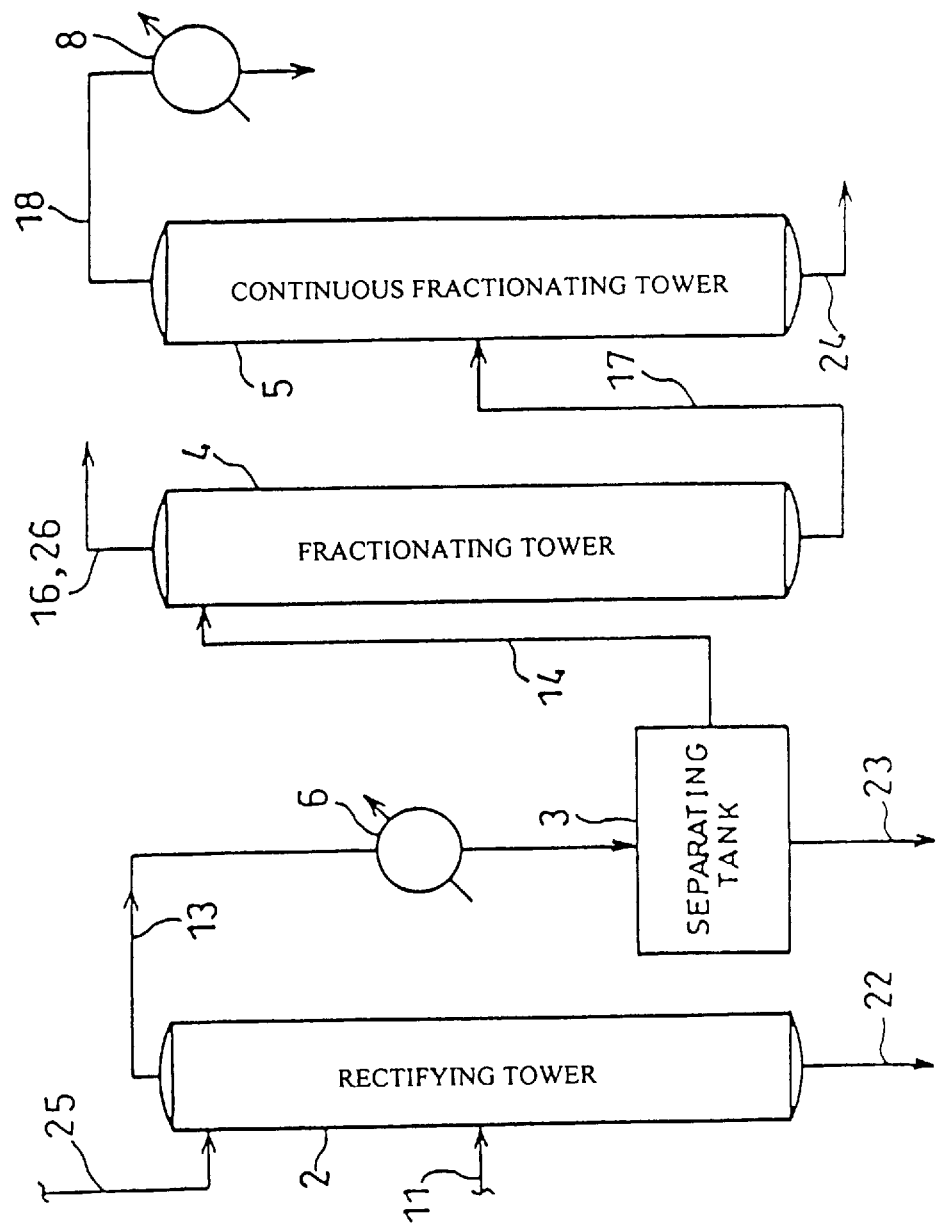
FIG. 3 is a block diagram showing a schematic structure of a distillation apparatus suitably used for a method of recovering ethylene sulfide in accordance with a further example embodiment of the present invention.

Further, as shown in FIG. 3, the distillation apparatus may be arranged in such a manner that the pipe 15 (FIG. 1) connecting the separating tank 3 and the continuous fractionating tower 2 in the vicinity of its overhead portion is replaced with a pipe 25 to steadily supply a hydrophobic organic compound of the same kind as the one contained in the solution to the continuous fractionating tower 2 in the vicinity of its overhead portion. In other words, the pipe 25 may be provided to connect an unillustrated hydrophobic organic compound supply tank to the continuous fractionating tower 2 in the vicinity of its overhead portion. Note that the hydrophobic organic compound supply tank steadily supplies the hydrophobic organic compound to the continuous fractionating tower 2.

When the above structure is adopted, a part of the oil layer is not returned, but a new hydrophobic organic compound of the same kind as the one contained in the solution is supplied to the continuous fractionating tower 2. When the new hydrophobic organic compound is supplied to the continuous fractionating tower 2 in the vicinity of its overhead portion in the above manner, the continuous fractionating tower 2 can obtain the similar effects to those obtained when it carries out a typical reflux operation. As a result, the distillate from the continuous fractionating tower 2 is completely free of the compound having a high boiling point, and the water distilled out as distillate is never returned to the continuous fractionating tower 2. Therefore, the polymerization reaction of ethylene sulfide, namely, the production of a polymer, can be suppressed in the continuous fractionating tower 2.

As has been explained, in the method of recovering ethylene sulfide of the present invention, a hydrous solution containing ethylene sulfide, the hydrophobic organic compound, and compound having a high boiling point is distilled continuously by the continuous fractionating tower 2 to distill out ethylene sulfide with the hydrophobic organic compound and water as distillate. Since ethylene sulfide can be separated from the compound having a high boiling point, the loss of ethylene sulfide by an addition reaction and a polymerization reaction can be reduced.

Also, in the method of recovering ethylene sulfide of the present invention, the distillate from the continuous fractionating tower 2 is allowed to stand in the separating tank 3 to separate into the oil and water layers. As a result, ethylene sulfide hardly touches water, thereby suppressing the polymerization reaction of ethylene sulfide, namely, the production of a polymer.

In addition, in the method of recovering ethylene sulfide of the present invention, a part of the oil layer is returned to the overhead portion of the continuous fractionating tower 2, thereby making the distillate from the continuous fractionating tower 2 completely free of the compound having a high boiling point. Moreover, of the oil and water layers contained in the distillate, the oil layer alone is returned to the continuous fractionating tower 2. Thus, water is never returned to the continuous fractionating tower 2 in practice, and therefore, the polymerization reaction of ethylene sulfide, namely, the production of a polymer, can be suppressed in the continuous fractionating tower 2.

Also, in the method of recovering ethylene sulfide of the present invention, the oil layer is supplied to the overhead portion of the fractionating tower 4, which in turn distills the oil layer continuously without carrying out the reflux operation to distill out water with a part of ethylene sulfide while releasing a mixture of ethylene sulfide and the hydrophobic organic compound from the bottom. Thus, since the time water remains in the fractionating tower 4 can be reduced, the polymerization reaction of ethylene sulfide, namely, the production of a polymer, can be suppressed in the fractionating tower 4.

Further, in the method of recovering ethylene sulfide of the present invention, the bottom product from the fractionating tower 4 is rectified by the rectifying tower 5 to distill out ethylene sulfide, thereby making it possible to isolate and purify ethylene sulfide.

Furthermore, in the method of recovering ethylene sulfide of the present invention, a new solution used as the stock solution and the distillate from the fractionating tower 4 are steadily supplied to the tank 1. Accordingly, the composition of the solution supplied to the continuous fractionating tower 2 can be maintained at a specific ratio. Consequently, the distillation system becomes stable and the distillation operation can be carried out in a stable manner. Also, since ethylene sulfide contained in the distillate from the fractionating tower 4 is supplied to the continuous fractionating tower 2 again, the recovery percentage of ethylene sulfide can be further improved.

Also, in the method of recovering ethylene sulfide of the present invention, a new solution used as the stock solution is steadily supplied to the tank 1, while the distillate from the fractionating tower 4 is steadily supplied to the separating tank 3. Accordingly, the composition of the oil layer supplied to the fractionating tower 4 can be maintained at a specific ratio. Consequently, the distillation system becomes stable and the distillation operation can be carried out in a stable manner. Also, since ethylene sulfide contained in the distillate from the fractionating tower 4 is supplied to the fractionating tower 4 again, the recovery percentage of ethylene sulfide can be further improved.

Further, in the method of recovering ethylene sulfide of the present invention, a hydrophobic organic compound of the same kind as the one contained in the solution is steadily supplied to the overhead portion of the continuous fractionating tower 2. Consequently, the distillate from the continuous fractionating tower 2 is completely free of the compound having a high boiling point. Also, water distilled out as distillate is never returned to the continuous fractionating tower 2. Therefore, the polymerization reaction of ethylene sulfide, namely, the production of a polymer, can be suppressed in the continuous fractionating tower 2.

In short, according to the above-explained method of recovering ethylene sulfide, the polymerization reaction of ethylene sulfide can be suppressed, and therefore, ethylene sulfide can be separated and recovered continuously in an efficient and stable manner.

Next, a method of dehydrating ethylene sulfide will be explained in the following.

In the method of dehydrating ethylene sulfide of the present invention, hydrous ethylene sulfide and a mixed solution containing hydrous ethylene sulfide and the hydrophobic organic compound are subject to distillation operation. The above mixed solution can be readily produced by distilling the reactant solution obtained by the above conventional ethylene sulfide producing method, and mixing the hydrophobic organic compound with the resulting distillate containing ethylene sulfide and water. Examples of the reactant solution include, but are not limited to, the scavenge solution, preserved solution and the like explained above in connection with the method of recovering ethylene sulfide.

A method of isolating ethylene sulfide by continuously dehydrating the above solution, namely, a dehydrating method will be explained. To begin with, an example distillation apparatus suitably used for dehydrating hydrous ethylene sulfide will be explained with reference to FIG. 4.

Figure 4:
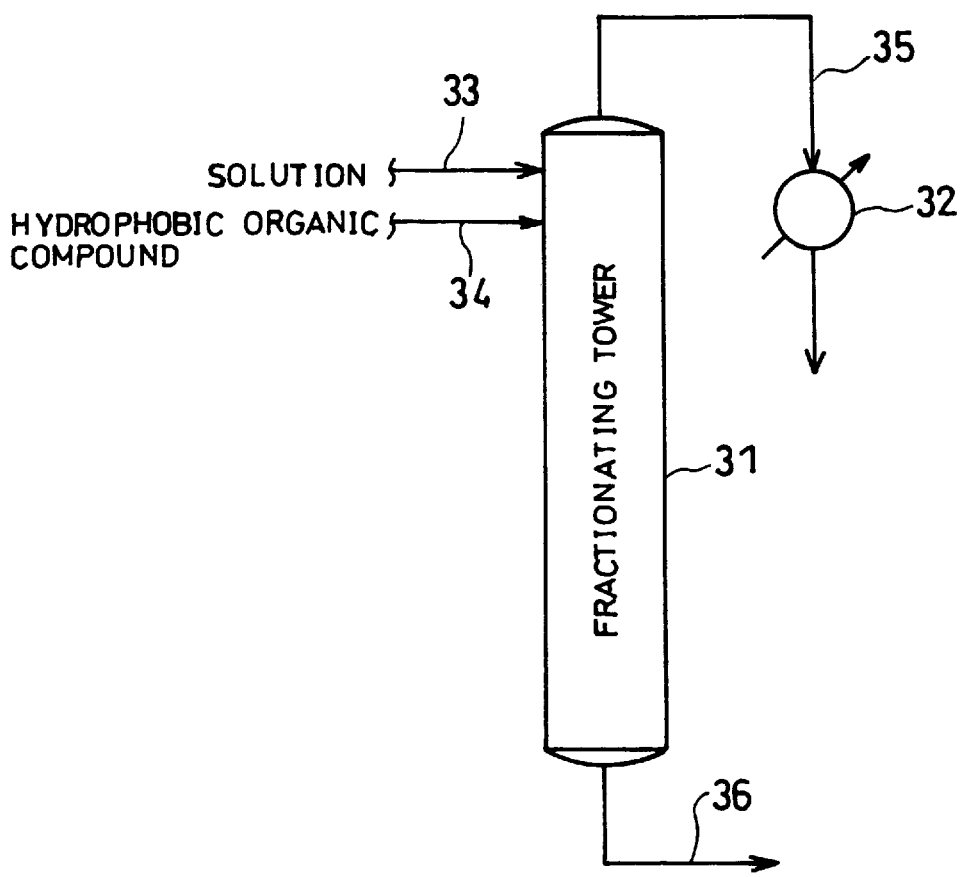
FIG. 4 is a block diagram showing a schematic structure of a distillation apparatus suitably used for a method of dehydrating ethylene sulfide in accordance with still another example embodiment of the present invention.

As shown in FIG. 4, the above distillation apparatus comprises a fractionating tower 31, a condenser 32, etc. The fractionating tower 31 is a multi-stage fractionating tower which does not carry out a reflux operation, and instead, distills the solution continuously by setting the reflux ratio to zero in practice to dehydrate the solution completely. In short, the fractionating tower 31 dehydrates ethylene sulfide.

The fractionating tower 31 is connected to, for example, an unillustrated solution supply tank through a pipe 33 and to an unillustrated hydrophobic organic compound supply tank through a pipe 34 both in the vicinity of its overhead portion. The overhead portion of the fractionating tower 31 is connected to, for example, an unillustrated distillate reservoir tank through a pipe 35 and the condenser 32. On the other hand, the bottom portion of the fractionating tower 31 is connected to, for example, an unillustrated rectifying tower through a pipe 36.

The solution is steadily supplied to the fractionating tower 31 in the vicinity of its overhead portion through the pipe 33, while the hydrophobic organic compound is steadily supplied to the same through the pipe 34. On the other hand, the fractionating tower 31 distills out water with a part of ethylene sulfide as distillate while releasing a mixture of ethylene sulfide and the hydrophobic organic compound as the bottom product.

The condenser 32 is provided at a predetermined position of the pipe 35 to condense and liquefy a gas (distillate) distilled out from the fractionating tower 31.

The solution supply tank constantly reserves a predetermined quantity of the above solution and supplies the same to the fractionating tower 31. Likewise, the hydrophobic organic compound supply tank constantly reserves a predetermined quantity of the hydrophobic organic compound and supplies the same to the fractionating tower 31. The distillate reservoir tank reserves the above distillate. The rectifying tower rectifies the above mixture to distill out ethylene sulfide as distillate and release the hydrophobic organic compound as the bottom product. In short, the rectifying tower isolates and purifies ethylene sulfide.

Although it is not illustrated in the drawing, the distillation apparatus further comprises components necessary for the distillation operation other than the aforementioned components, for example, a heat exchanger, and a pump.

Next, a method of dehydrating ethylene sulfide using the above-structured distillation apparatus will be explained.

To begin with, the solution and hydrophobic organic compound are steadily supplied to the fractionating tower 31 in the vicinity of its overhead portion from the solution supply tank and hydrophobic organic compound supply tank, respectively. Then, the solution and hydrophobic organic compound supplied to the fractionating tower 31 are continuously distilled to distill out a part of ethylene sulfide and water as distillate from the overhead. The rest (substantial part) of ethylene sulfide and the hydrophobic organic compound are released from the bottom as the bottom product. The solution is supplied to the fractionating tower 31 in the vicinity of its overhead portion, and the fractionating tower 31 continuously distills the solution by setting the reflux ratio to zero in practice to dehydrate the solution completely and quickly. Consequently, the time water remains in the fractionating tower 31 can be reduced. Thus, ethylene sulfide can be dehydrated efficiently while the polymerization reaction of the same, namely, the production of a polymer, is suppressed in the fractionating tower 31.

The composition of the distillate from the fractionating tower 31, or the composition ratio of the aforementioned two elements, is determined by the distillation conditions in the fractionating tower 31, such as the temperatures at the overhead and bottom, and the number of stages in the tower. In other words, changing the distillation conditions in the fractionating tower 31 can change the composition of the distillate and bottom product of the fractionating tower 31. The distillation in the fractionating tower 31 can be carried out under either normal or reduced pressure. Note that the distillate from the fractionating tower 31 hardly contains the hydrophobic organic compound.

Subsequently, the bottom product from the fractionating tower 31 is steadily supplied to the rectifying tower. The bottom product supplied to the rectifying tower is continuously rectified to distill out ethylene sulfide from the overhead as distillate and release the hydrophobic organic compound from the bottom as the bottom product. The rectifying tower carries out a typical rectifying operation. Note that the distillation conditions in the rectifying tower, such as the temperatures at the overhead and bottom, the number of stages in the tower, and reflux ratio, are not especially limited.

The solution is dehydrated efficiently by the above distillation operation and dry ethylene sulfide can be obtained in a stable manner.

Next, an example distillation apparatus suitably used for dehydrating the mixed solution will be explained in the following with reference to FIG. 5.

Figure 5:
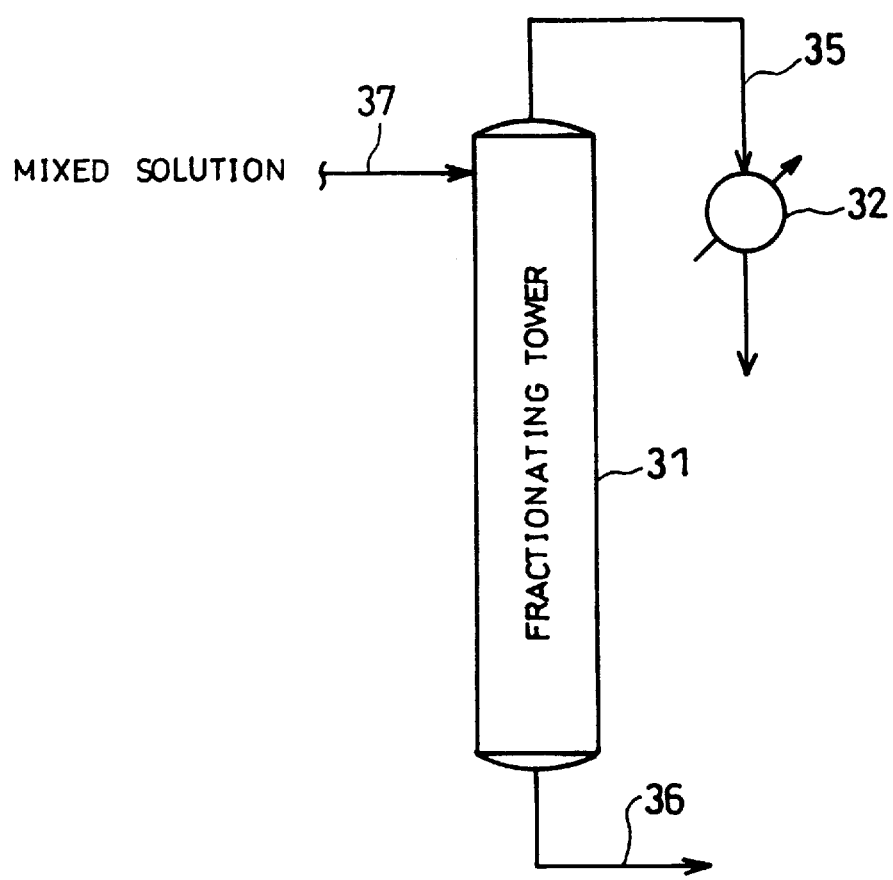
FIG. 5 is a block diagram showing a schematic structure of a distillation apparatus suitably used for a method of dehydrating ethylene sulfide in accordance with still another example embodiment of the present invention.

As shown in FIG. 5, the distillation apparatus herein includes a pipe 37 instead of the pipes 33 and 34 compared with the counterpart of FIG. 4. To be more specific, the fractionating tower 31 is connected to, for example, an unillustrated mixed solution supply tank through the pipe 37 in the vicinity of its overhead portion, so that the mixed solution is steadily supplied to the fractionating tower 31 in the vicinity of its overhead portion through the pipe 37. The mixed solution supply tank constantly reserves a predetermined quantity of the mixed solution and supplies the same to the fractionating tower 31. The rest of the structure of the distillation apparatus is identical with that of the counterpart of FIG. 4.

Next, a method of dehydrating ethylene sulfide using the above-structured distillation apparatus will be explained.

To begin with, the mixed solution is steadily supplied from the mixed solution supply tank to the fractionating tower 31 in the vicinity of its overhead portion. The mixed solution supplied to the fractionating tower 31 is distilled continuously to distill out a part of ethylene sulfide and water as distillate form the overhead. The rest (substantial part) of ethylene sulfide and the hydrophobic organic compound are released from the bottom as the bottom product. The distillation operation thereafter is identical with the distillation operation using the distillation apparatus of FIG. 4.

The mixed solution is dehydrated efficiently by the above distillation operation, and as a result, dry ethylene sulfide can be obtained in a stable manner. Note that the structure of the distillation apparatus is not limited to the structures of FIGS. 4 and 5, and the distillation apparatus can be of other structures. For example, the distillation apparatus of the structure shown in FIG. 5 may be modified in such a manner that the fractionating tower 31 includes an unillustrated pipe for steadily supplying a hydrophobic organic compound of the same kind as the one contained in the mixed solution. In other words, the distillation operation can be carried out while the mixed solution and the hydrophobic organic compound are steadily supplied to the fractionating tower 31.

As has been explained, in the method of dehydrating ethylene sulfide of the present invention, hydrous ethylene sulfide and the hydrophobic organic compound are supplied to the fractionating tower 31 to continuously distill out water with a part of ethylene sulfide and release the mixture of ethylene sulfide and hydrophobic organic compound from the bottom of the fractionating tower 31. Also, in the method of dehydrating ethylene sulfide of the present invention, ethylene sulfide and hydrophobic organic compound are supplied to the fractionating tower 31 in the vicinity of its overhead portion, and distilled without being subjected to a reflux operation. Further, in the method of dehydrating ethylene sulfide of the present invention, the mixed solution containing hydrous ethylene sulfide and the hydrophobic organic compound is steadily supplied to the fractionating tower 31 to be distilled continuously, so that water is distilled out with a part of ethylene sulfide, while the mixture of ethylene sulfide and the hydrophobic organic compound is released from the bottom of the fractionating tower 31. Also, in the method of dehydrating ethylene sulfide of the present invention, the mixed solution is supplied to the fractionating tower 31 in the vicinity of its overhead portion to distill the mixed solution without carrying a reflux operation. Moreover, in the method of dehydrating ethylene sulfide of the present invention, a hydrophobic organic compound of the same kind as the one contained in the solution is steadily supplied to the fractionating tower 31.

Thus, the time water remains in the fractionating tower 31 can be reduced. Consequently, it has become possible to dehydrate ethylene sulfide efficiently while suppressing polymerization reaction of the same, namely, the production of a polymer, in the fractionating tower 31.

In addition, in the method of dehydrating ethylene sulfide of the present invention, ethylene sulfide is isolated from the bottom product from the fractionating tower 31 by distilling the bottom product. Consequently, ethylene sulfide can be purified.

In short, according to the above dehydrating method, ethylene sulfide is dehydrated efficiently while suppressing the polymerization reaction of the same, and as a result, dry ethylene sulfide can be obtained in a stable manner.

The present invention will be detailed by ways of examples below; however, the present invention is not limited to these examples. Note that Examples 1 through 4 relate to the method of recovering ethylene sulfide and Examples 5 through 7 relate to the method of dehydrating ethylene sulfide.

(EXAMPLE 1)

Ethylene sulfide is recovered continuously using the distillation apparatus of FIG. 1. However, the pipe 16 provided at the overhead portion of the fractionating tower 4 is not connected to the tank 1, but to an unillustrated recovering tank. In other words, the distillate from the fractionating tower 4 is not returned to the tank 1, but recovered by the recovering tank. Also, toluene is used as the hydrophobic organic compound.

The continuous fractionating tower 2 used herein comprises a glass tube having a bore diameter of 50 mm filled with a 5 mm$\phi$ stainless dickson packing of 50 cm long at its enriching section, and the 5 mm$\phi$ stainless dickson packing of 80 cm long at its recovering section. The fractionating tower 4 used herein comprises a glass tube having a bore diameter of 30 mm filled with a 5 mm$\phi$ stainless dickson packing of 40 cm long at its recovering section. Likewise, the rectifying tower 5 used herein comprises a glass tube having a bore diameter of 30 mm filled with a 5 mm$\phi$ stainless dickson packing of 30 cm long at its enriching section and the 5 mm$\phi$ stainless dickson packing of 50 cm long at its recovering section. The distillate is allowed to stand inside the separating tank 3 while its temperature being kept at 5° C.

The continuous fractionating tower 2, fractionating tower 4, and rectifying tower 5 are operated under normal pressure. A quantity of the oil layer returned to the continuous fractionating tower 2 from the separating tank 3 is adjusted to set the reflux ratio of the continuous fractionating tower 2 to five. Also, the rectifying tower 5 is arranged to operate at a reflux ratio of seven. Note that since the fractionating tower 4 does not carry out the reflux operation, the reflux ratio of the same is zero in practice.

The quantity of the solution supplied to the continuous fractionating tower 2 per unit hour (hereinafter, referred to as supplying rate), the quantity of distillate distilled out from the continuous fractionating tower 2 per unit hour (hereinafter, referred to as distilling rate), the quantity of the bottom product released from the continuous fractionating tower 2 per unit hour (hereinafter, referred to as bottom releasing rate), a supplying rate of the oil layer to the fractionating tower 4, a distilling rate of the distillate distilled out from the fractionating tower 4, a bottom releasing rate of the bottom product from the fractionating tower 4, a supplying rate of the bottom product supplied from the fractionating tower 4 to the rectifying tower 5, a distilling rate of the distillate distilled out from the rectifying tower 5, and a bottom releasing rate of the bottom product released from the rectifying tower S are set forth in TABLE 1 below together with the their respective compositions.

TABLE 1

| TOWER NO. | RATE (BTM = BOTTOM) | COMPOSITION | | | |
|---|---|---|---|---|---|
| | | ETHYLENE SULFIDE (g/hr) | TOLUENE (g/hr) | HIGH-BOILING POINT COMPOUND (g/hr) | WATER (g/hr) |
| 2 | SUPPLYING | 248 | 740 | 6 | 2 |
| | DISTILLING | 247 | 325 | 0 | 2 |
| | BTM RELEASING | 0 | 415 | 7 | 0 |
| 4 | SUPPLYING | 247 | 325 | 0 | 1.2 |
| | DISTILLING | 25 | 5 | 0 | 1.2 |
| | BTM RELEASING | 222 | 320 | 0 | 0 |
| 5 | SUPPLYING | 222 | 320 | 0 | 0 |
| | DISTILLING | 222 | 1 | 0 | 0 |
| | BTM RELEASING | 0 | 319 | 0 | 0 |

Note that the distillate remains in the continuous fractionating tower 2 for five hours, and the quantity of the water layer separated by the separating tank 3 per unit hour is 0.8 g/hr, meaning that 40 wt % of water in the distillate is separated as the water layer.

TABLE 1 reveals that: (1) in the continuous fractionating tower 2, most of ethylene sulfide in the solution is distilled out with toluene as distillate, while the compound having a high boiling point is completely released with the rest of toluene as the bottom product; and (2) in the fractionating tower 4, water in the oil layer is completely distilled out with a part of ethylene sulfide and a small quantity of toluene as distillate. Note that the quantity of ethylene sulfide distilled out with water slightly exceeds the needed quantity to produce an azeotrope.

Ethylene sulfide recovered continuously by the above distillation apparatus, or by the recovering method of the present example, is 99.6 wt % pure, and the impurity contained therein is toluene.

A ratio of ethylene sulfide distilled out from the rectifying tower 5 to ethylene sulfide supplied to the continuous fractionating tower 2 in quantity, namely, the recovery percentage of ethylene sulfide, is 89.5 percent by weight. A ratio of ethylene sulfide distilled out from the fractionating tower 4 to ethylene sulfide supplied to the same in quantity, namely, the recovery percentage of ethylene sulfide by the unillustrated recovering tank is 9.1 percent by weight.

(EXAMPLE 2)

Ethylene sulfide is recovered continuously using the distillation apparatus of FIG. 3. Like in Example 1, the distillate from the fractionating tower 4 is not returned to the tank 1, but recovered by the recovering tank, and toluene is used as the hydrophobic organic compound. Further, each of the continuous fractionating tower 2, fractionating tower 4, and rectifying tower 5 is of the same structure as their respective counterparts of Example 1, and the distillate is allowed to stand inside the separating tank 3 while its temperature being kept at 5° C.

The continuous fractionating tower 2, fractionating tower 4, and rectifying tower 5 are operated under normal pressure. During the operation, toluene is steadily supplied to the continuous fractionating tower 2 from an unillustrated toluene supply tank (hydrophobic organic compound supply tank) at 350 g/hr. The rectifying tower 5 is operated at a reflux ratio of seven. Note that since the fractionating tower 4 does not carry out the reflux operation, the reflux ratio of the same is zero in practice.

The supplying rate, distilling rate, and bottom releasing rate of each of the continuous fractionating tower 2, fractionating tower 4, and rectifying tower 5 are set forth in TABLE 2 below with their respective compositions.

TABLE 2

| TOWER NO. | RATE (BTM = BOTTOM) | COMPOSITION | | | |
|---|---|---|---|---|---|
| | | ETHYLENE SULFIDE (g/hr) | TOLUENE (g/hr) | HIGH-BOILING POINT COMPOUND (g/hr) | WATER (g/hr) |
| 2 | SUPPLYING | 207 | 615 | 5 | 1.6 |
| | DISTILLING | 205 | 265 | 0 | 1.6 |
| | BTM RELEASING | 0 | 700 | 7 | 0 |
| 4 | SUPPLYING | 205 | 265 | 0 | 1.2 |
| | DISTILLING | 25 | 5 | 0 | 1.2 |
| | BTM RELEASING | 180 | 260 | 0 | 0 |
| 5 | SUPPLYING | 180 | 260 | 0 | 0 |
| | DISTILLING | 180 | 1 | 0 | 0 |
| | BTM RELEASING | 0 | 259 | 0 | 0 |

Note that the distillate remains in the continuous fractionating tower 2 for five hours, and the quantity of the water layer separated by the separating tank 3 per unit hour is 0.4 g/hr, meaning that 25 wt % of water in the distillate is separated as the water layer.

TABLE 2 reveals that: (1) in the continuous fractionating tower 2, most of ethylene sulfide in the solution is distilled out with toluene as distillate, while the compound having a high boiling point is completely released with the rest of toluene as the bottom product; and (2) in the fractionating tower 4, water in the oil layer is distilled out completely with a part of ethylene sulfide and a small quantity of toluene as distillate. Note that the quantity of ethylene sulfide distilled out with water slightly exceeds the needed quantity to produce an azeotrope.

Ethylene sulfide recovered continuously by the above distillation apparatus, or by the recovering method of the present example, is 99.5 wt % pure, and the impurity contained therein is toluene.

A ratio of ethylene sulfide distilled out from the rectifying tower 5 to ethylene sulfide supplied to the continuous fractionating tower 2 in quantity, namely, the recovery percentage of ethylene sulfide, is 87.0 percent by weight. A ratio of ethylene sulfide distilled out from the fractionating tower 4 to ethylene sulfide supplied to the same in quantity, namely, the recovery percentage of ethylene sulfide by the unillustrated recovering tank, is 12.1 percent by weight.

(EXAMPLE 3)

Ethylene sulfide is recovered continuously using the distillation apparatus of FIG. 2, and toluene is used as the hydrophobic organic compound. Further, each of the continuous fractionating tower 2, fractionating tower 4, and rectifying tower 5 is of the same structure as their respective counterparts of Example 1, and the distillate is allowed to stand inside the separating tank 3 while its temperature being kept at 5° C.

The continuous fractionating tower 2, fractionating tower 4, and rectifying tower 5 are operated under normal pressure. A quantity of the oil layer returned to the continuous fractionating tower 2 from the separating tank 3 is adjusted to set the reflux ratio of the continuous fractionating tower 2 to five. Also, the rectifying tower 5 is arranged to operate at a ref lux ratio of seven. Note that since the fractionating tower 4 does not carry out the reflux operation, the reflux ratio of the same is zero in practice.

The supplying rate, distilling rate, and bottom releasing rate of each of the continuous fractionating tower 2, fractionating tower 4, and rectifying tower 5 are set forth in TABLE 3 below with their respective compositions. Note that a quantity of the water layer separated by the separating tank 3 per unit hour is 2 g/hr.

TABLE 3

| TOWER NO. | RATE (BTM = BOTTOM) | COMPOSITION | | | |
|---|---|---|---|---|---|
| | | ETHYLENE SULFIDE (g/hr) | TOLUENE (g/hr) | HIGH-BOILING POINT COMPOUND (g/hr) | WATER (g/hr) |
| 2 | SUPPLYING | 248 | 740 | 6 | 2 |
| | DISTILLING | 247 | 325 | 0 | 2 |
| | BTM RELEASING | 0 | 415 | 7 | 0 |
| 4 | SUPPLYING | 272 | 330 | 0 | 1.3 |
| | DISTILLING | 25 | 5 | 0 | 1.3 |
| | BTM RELEASING | 247 | 325 | 0 | 0 |
| 5 | SUPPLYING | 247 | 325 | 0 | 0 |
| | DISTILLING | 247 | 2 | 0 | 0 |
| | BTM RELEASING | 0 | 323 | 0 | 0 |

Ethylene sulfide recovered continuously by the above distillation apparatus, or by the recovering method of the present example, is 99.2 wt % pure, and the impurity contained therein is toluene.

A ratio of ethylene sulfide distilled out from the rectifying tower 5 to ethylene sulfide supplied to the separating tank 3 in quantity, namely, the recovery percentage of ethylene sulfide, is 99.6 percent by weight.

(EXAMPLE 4)

Ethylene sulfide is continuously recovered using the distillation apparatus of FIG. 1, and toluene is used as the hydrophobic organic compound. Each of the continuous fractionating tower 2, fractionating tower 4, and rectifying tower 5 is of the same structure as their respective counterparts in Example 1, and the distillate is allowed to stand inside the separating tank 3 while its temperature being kept at 5° C.

Further, the stock solution (solution) is steadily supplied to the tank 1 from an unillustrated stock supply tank. To be more specific, ethylene sulfide, toluene and the compound having a high boiling point are supplied to the tank 1 at 248 g/hr, 735 g/hr, and 6 g/hr, respectively. Water separated from the solution in the tank 1 is released as occasion demands, so that the oil layer alone is supplied to the continuous fractionating tower 2 from the tank 1.

The continuous fractionating tower 2, fractionating tower 4, and rectifying tower 5 are operated under normal pressure. During the operation, a quantity of the oil layer returned to the continuous fractionating tower 2 from the separating tank 3 is adjusted to set the reflux ratio of the continuous fractionating tower 2 to five. Also, the rectifying tower 5 is arranged to operate at a reflux ratio of seven. Note that since the fractionating tower 4 does not carry out the reflux operation, the reflux ratio of the same is zero in practice.

The supplying rate, distilling rate, and bottom releasing rate of each of the continuous fractionating tower 2, fractionating tower 4, and rectifying tower 5 are set forth in TABLE 4 below with their respective compositions. Note that a quantity of the water layer separated by the separating tank 3 per unit hour is 0.7 g/hr.

TABLE 4

| TOWER NO. | RATE (BTM = BOTTOM) | COMPOSITION | | | |
|---|---|---|---|---|---|
| | | ETHYLENE SULFIDE (g/hr) | TOLUENE (g/hr) | HIGH-BOILING POINT COMPOUND (g/hr) | WATER (g/hr) |
| 2 | SUPPLYING | 275 | 750 | 6 | 2 |
| | DISTILLING | 271 | 325 | 0 | 2 |
| | BTM RELEASING | 0 | 425 | 10 | 0 |
| 4 | SUPPLYING | 271 | 325 | 0 | 1.3 |
| | DISTILLING | 27 | 5 | 0 | 1.3 |
| | BTM RELEASING | 244 | 320 | 0 | 0 |
| 5 | SUPPLYING | 244 | 320 | 0 | 0 |
| | DISTILLING | 244 | 1 | 0 | 0 |
| | BTM RELEASING | 0 | 319 | 0 | 0 |

Ethylene sulfide recovered continuously by the above distillation apparatus, or by the recovering method of the present example, is 99.6 wt % pure, and the impurity contained therein is toluene.

A ratio of ethylene sulfide distilled out from the rectifying tower 5 to ethylene sulfide in the stock solution supplied to the tank 1 in quantity, namely, the recovery percentage of ethylene sulfide, is 98.4 percent by weight.

It is apparent from Examples 1 through 4 that the recovering methods of these four examples can suppress the polymerization reaction of ethylene sulfide, thereby making it possible to separate and recover ethylene sulfide continuously in an efficient and stable manner.

(EXAMPLE 5)

Hydrous ethylene sulfide is continuously dehydrated using the distillation apparatus of FIG. 4. Ethylene sulfide containing 0.2 wt % of water is used as the solution, and toluene is used as the hydrophobic organic compound.

The fractionating tower 31, which is operated under normal pressure, comprises a glass tube having a bore diameter of 30 mm filled with a 5 mm$\phi$ stainless dickson packing of 40 cm long at its recovering section. Since the fractionating tower 31 does not carry out a reflux operation, the reflux ratio of the same is zero in practice.

A quantity of the solution supplied to the fractionating tower 31 per unit hour (hereinafter, referred to as a solution supplying rate) is 400 g/hr. Also, a quantity of the hydrophobic organic compound supplied to the fractionating tower 31 per unit hour (hereinafter, referred to as hydrophobic organic compound supplying rate) is 300 g/hr.

As a result, a quantity of distillate distilled out from the fractionating tower 31 per unit hour (hereinafter referred to as a distilling rate) is specified as follows: water at 0.8 g/hr, ethylene sulfide at 38 g/hr, and toluene at 2 g/hr. Also, a quantity of the bottom product released from the fractionating tower 31 per unit hour (hereinafter, referred to as a bottom releasing rate) is specified as follows: ethylene sulfide at 362 g/hr and toluene at 298 g/hr. Note that no water is contained in the bottom product herein. The solution is distilled for about consecutive 100 hours under the above conditions, and the polymerization reaction of ethylene sulfide, namely, the production of a polymer, is not acknowledged in the fractionating tower 31.

It is obvious from the above result that the water in the solution is completely distilled out with a part of ethylene sulfide and a small quantity of toluene as distillate from the fractionating tower 31. Note that ethylene sulfide can be readily isolated and purified by distilling the bottom product from the fractionating tower 31.

(EXAMPLE 6)

Hydrous ethylene sulfide is continuously dehydrated using the distillation apparatus identical with the one used in Example 5. Ethylene sulfide containing 0.2 percent by weight of water is used as the solution, and mesitylene (1,3,5-trimethyl benzene) is used as the hydrophobic organic compound. Note that the distillation is carried out under the same conditions as those of Example 5.

Here, the solution supplying rate is 400 g/hr, and the hydrophobic organic compound supplying rate is 200 g/hr. As a result, the distilling rates of water, ethylene sulfide, and mesitylene are 0.8 g/hr, 45 g/hr, and 0.5 g/hr, respectively. The bottom releasing rates of ethyl sulfide and mesitylene are 355 g/hr and 199.5 g/hr, respectively. Note that no water is contained in the bottom product herein. The solution is distilled for about consecutive 100 hours under the above conditions, and the polymerization reaction of ethylene sulfide, namely, the production of a polymer, is not acknowledged in the fractionating tower 31.

It is obvious from the above result that water in the solution is distilled out completely with a part of ethylene sulfide and a small quantity of mesitylene as distillate from the fractionating tower 31. Note that ethylene sulfide can be readily isolated and purified by distilling the bottom product from the fractionating tower 31.

(EXAMPLE 7)

Hydrous ethylene sulfide is continuously dehydrated using the distillation apparatus of FIG. 5. Here, a mixed solution of 0.1 percent by weight of water, 45.6 percent by weight of ethylene sulfide, and 54.3 percent by weight of toluene serving as the hydrophobic organic compound is used as the solution. Note that the fractionating tower 31 is of the same structure as the counterpart in Example 5, and the distillation operation is carried out under the same conditions as those in Example 5.

A quantity of the mixed solution supplied to the fractionating tower 31 per unit hour is 700 g/hr. As a result, the distilling rates of water, ethylene sulfide, and toluene are 0.7 g/hr, 35.7 g/hr, and 1.6 g/hr, respectively. The bottom releasing rates of ethylene sulfide and toluene are 283.5 g/hr and 378.5 g/hr, respectively. Note that no water is contained in the bottom product herein. The solution is distilled for about consecutive 100 hours under the above conditions, and the polymerization reaction of ethylene sulfide, namely, the production of a polymer, is not acknowledged in the fractionating tower 31.

It is obvious from the above result that water in the solution is distilled out completely with a part of ethylene sulfide and a small quantity of toluene as distillate from the fractionating tower 31. Note that ethylene sulfide can be readily isolated and purified by distilling the bottom product from the fractionating tower 31.

It is obvious from Examples 5 through 7 that the dehydrating methods of these three examples can dehydrate ethylene sulfide efficiently while suppressing the polymerization reaction of the same, thereby making it possible to obtain dry ethylene sulfide in a stable manner.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

POSSIBLE INDUSTRIAL APPLICATION

The method of recovering ethylene sulfide of the present invention can suppress the polymerization reaction of ethylene sulfide, thereby making it possible to separate and recover ethylene sulfide continuously in an efficient and stable manner. The above method can also prevent clogging of the fractionating towers, pipes, etc.

Also, the method of dehydrating ethylene sulfide of the present invention can dehydrate ethylene sulfide efficiently while suppressing the polymerization reaction of the same, thereby making it possible to obtain dry ethylene sulfide in a stable manner.

What is claimed is:

1. A method of recovering ethylene sulfide comprising a step of continuously distilling, using a first fractionating tower, a hydrous solution containing ethylene sulfide, a hydrophobic organic compound having a higher boiling point than ethylene sulfide, and a compound having a higher boiling point than said hydrophobic organic compound, said hydrophobic solvent being inactive to ethylene sulfide and to said higher boiling point compound, so that ethylene sulfide is distilled out with said hydrophobic organic compound and water.

2. The method of recovering ethylene sulfide as defined in claim 1, wherein said distilling step using said first fractionating tower includes a step of steadily supplying a hydrophobic organic compound of a same kind as said hydrophobic organic compound to a overhead portion of said first fractionating tower.

3. The method of recovering ethylene sulfide as defined in claim 1, wherein said distilling step using said first fractionating tower includes a step of steadily supplying said solution to a middle stage portion of said first fractionating tower.

4. The method of recovering ethylene sulfide as defined in claim 1, wherein said distilling step using said first fractionating tower is carried out under one of normal pressure and reduced pressure.

5. The method of recovering ethylene sulfide as defined in claim 1, wherein said hydrophobic organic compound is at least one kind of hydrocarbons selected from the group consisting of aromatic hydrocarbons and aliphatic hydrocarbons.

6. The method of recovering ethylene sulfide as defined in claim 1, wherein said hydrophobic organic compound is a hydrocarbon having six carbon atoms or more.

7. The method of recovering ethylene sulfide as defined in claim 1, wherein a quantity of ethylene sulfide contained in distillate from said first fractionating tower is 75 percent by weight or less.

8. The method of recovering ethylene sulfide as defined in claim 1 further comprising a subsequent step to said distilling step using said first fractionating tower, said subsequent step being a step of allowing distillate from said first fractionating tower to stand, so that said distillate separates into an oil layer and a water layer.

9. The method of recovering ethylene sulfide as defined in claim 8 further comprising a subsequent step to said step of allowing said distillate from said first fractionating tower to stand, said subsequent step being a step of returning a part of said oil layer to an overhead portion of said first fractionating tower.

10. The method of recovering ethylene sulfide as defined in claim 8 further comprising a subsequent step to said step of allowing said distillate from said first fractionating tower to stand, said subsequent step being a step of supplying said oil layer to an overhead portion of a second fractionating tower to be distilled continuously by said second fractionating tower without being subject to a reflux operation, so that water is distilled out with a part of ethylene sulfide and a mixture of ethylene sulfide and said hydrophobic organic compound is released from a bottom of said second fractionating tower.

11. The method of recovering ethylene sulfide as defined in claim 10, wherein said distilling step using said second fractionating tower is carried out under one of normal pressure and reduced pressure.

12. The method of recovering ethylene sulfide as defined in claim 10 further comprising a subsequent step to said distilling step using said second fractionating tower, said subsequent step being a step of distilling a bottom product from said second fractionating tower using a third fractionating tower to distill out ethylene sulfide.

13. The method of recovering ethylene sulfide as defined in claim 10 further comprising a subsequent step to said distilling step using said second fractionating tower, said subsequent step being a step of steadily supplying a new solution as a stock solution and distillate from said second fractionating tower to a tank which steadily supplies said solution to said first fractionating tower.

14. The method of recovering ethylene sulfide as defined in claim 10 further comprising a subsequent step to said distilling step using said second fractionating tower, said subsequent step being a step of steadily supplying a new solution as a stock solution to a tank which steadily supplies said solution to said first fractionating tower, and steadily supplying distillate from said second fractionating tower to a separating tank in which distillate from said first fractionating tower is allowed to separate into an oil layer and a water layer.

15. A method of dehydrating ethylene sulfide comprising a step of steadily supplying hydrous ethylene sulfide and a hydrophobic organic compound that is inactive to ethylene sulfide and has a higher boiling point than ethylene sulfide to a fractionating tower to be distilled continuously, so that water is distilled with a part of ethylene sulfide while a mixture of ethylene sulfide and said hydrophobic organic compound is released from a bottom of said fractionating tower.

16. The method of dehydrating ethylene sulfide as defined in claim 15, wherein said distilling step using said fractionating tower includes a step of supplying ethylene sulfide and said hydrophobic organic compound to an overhead portion of said fractionating tower to be distilled without being subjected to a reflux operation.

17. The method of dehydrating ethylene sulfide as defined in claim 15, wherein said distilling step using said fractionating tower is carried out under one of normal pressure and reduced pressure.

18. The method of dehydrating ethylene sulfide as defined in claim 15, wherein said hydrophobic organic compound is at least one kind of hydrocarbons selected from a group consisting of aromatic hydrocarbons and aliphatic hydrocarbons.

19. The method of dehydrating ethylene sulfide as defined in claim 15, wherein said hydrophobic organic compound is a hydrocarbon having six carbon atoms or more.

20. The method of dehydrating ethylene sulfide as defined in claim 15 further comprising a subsequent step to said distilling step using said fractionating tower, said subsequent step being a step of distilling a bottom product from said fractionating tower to isolate ethylene sulfide.

21. A method of dehydrating ethylene sulfide comprising a step of steadily supplying a solution containing hydrous ethylene sulfide and a hydrophobic organic compound that is inactive to ethylene sulfide and has a higher boiling point than ethylene sulfide to a fractionating tower to be distilled continuously, so that water is distilled out with a part of ethylene sulfide while a mixture of ethylene sulfide and said hydrophobic organic compound is released from a bottom of said fractionating tower.

22. The method of dehydrating ethylene sulfide as defined in claim 21, wherein said distilling step using said fractionating tower includes a step of supplying said solution to an overhead portion of said fractionating tower to be distilled without being subjected to a reflux operation.

23. The method of dehydrating ethylene sulfide as defined in claim 21, wherein said distilling step using said fractionating tower includes a step of steadily supplying a hydrophobic organic compound of a same kind as said hydrophobic organic compound to said fractionating tower.

24. The method of dehydrating ethylene sulfide as defined in claim 21, wherein said distilling step using said fractionating tower is carried out under one of normal pressure and reduced pressure.

25. The method of dehydrating ethylene sulfide as defined in claim 21, wherein said hydrophobic organic compound is at least one kind of hydrocarbons selected from a group consisting of aromatic hydrocarbons and aliphatic hydrocarbons.

26. The method of dehydrating ethylene sulfide as defined in claim 21, wherein said hydrophobic organic compound is a hydrocarbon having six carbon atoms or more.

27. The method of dehydrating ethylene sulfide as defined in claim 21 further comprising a subsequent step to said distilling step using said fractionating tower, said subsequent step being a step of distilling a bottom product from said fractionating tower to isolate ethylene sulfide.

28. The method of recovering ethylene sulfide as defined in claim 1, wherein said hydrophobic solvent is at least one compound selected from the group consisting of aromatic hydrocarbons, halogen-containing aromatic compounds, aliphatic hydrocarbons, halogen-containing aliphatic compounds, ether compounds, ketone compounds and ester compounds.

29. The method of dehydrating ethylene sulfide as defined in claim 15, wherein said hydrophobic solvent is at least one compound selected from the group consisting of aromatic hydrocarbons, halogen-containing aromatic compounds, aliphatic hydrocarbons, halogen-containing aliphatic compounds, ether compounds, ketone compounds and ester compounds.

30. The method of dehydrating ethylene sulfide as defined in claim 21, wherein said hydrophobic solvent is at least one compound selected from the group consisting of aromatic hydrocarbons, halogen-containing aromatic compounds, aliphatic hydrocarbons, halogen-containing aliphatic compounds, ether compounds, ketone compounds and ester compounds.

31. The method of recovering ethylene sulfide as defined in claim 28, wherein said aromatic hydrocarbon is selected from the group consisting of benzene, toluene, xylene, pseudocumene, diethylbenzene and tetralin; said halogen-containing aromatic compound is selected from the group consisting of fluorobenzene, hexafluorobenzene, chlorobenzene, and chlorotoluene; said aliphatic hydrocarbon is selected from the group consisting of hexane, decane, isooctane, cyclohexane, and methylcyclohexane; said halogen-containing aliphatic compound is selected from the group consisting of chloroform, carbon tetrachloride, 1,2-dichloroethane, and fluorocyclohexane; said ether compound is selected from the group consisting of dipropyl ether, butylmethyl ether, and phenylmethyl ether; said ketone compound is selected from the group consisting of 3-hexanone, 2-heptanone, cyclohexanone, and phenylmethylketone; and said ester compound is selected from the group consisting of phenyl acetate and methyl benzoate.

32. The method of dehydrating ethylene sulfide as defined in claim 29, wherein said aromatic hydrocarbon is selected from the group consisting of benzene, toluene, xylene, pseudocumene, diethylbenzene and tetralin; said halogen-containing aromatic compound is selected from the group consisting of fluorobenzene, hexafluorobenzene, chlorobenzene, and chlorotoluene; said aliphatic hydrocarbon is selected from the group consisting of hexane, decane, isooctane, cyclohexane, and methylcyclohexane; said halogen-containing aliphatic compound is selected from the group consisting of chloroform, carbon tetrachloride, 1,2-dichloroethane, and fluorocyclohexane; said ether compound is selected from the group consisting of dipropyl ether, butylmethyl ether, and phenylmethyl ether; said ketone compound is selected from the group consisting of 3-hexanone, 2-heptanone, cyclohexanone, and phenylmethylketone; and said ester compound is selected from the group consisting of phenyl acetate and methyl benzoate.

33. The method of dehydrating ethylene sulfide as defined in claim 30, wherein said aromatic hydrocarbon is selected from the group consisting of the group benzene, toluene, xylene, pseudocumene, diethylbenzene and tetralin; said halogen-containing aromatic compound is selected from the group consisting of fluorobenzene, hexafluorobenzene, chlorobenzene, and chlorotoluene; said aliphatic hydrocarbon is selected from the group consisting of hexane, decane, isooctane, cyclohexane, and methylcyclohexane; said halogen-containing aliphatic compound is selected from the group consisting of chloroform, carbon tetrachloride, 1,2-dichloroethane, and fluorocyclohexane; said ether compound is selected from the group consisting of dipropyl ether, butylmethyl ether, and phenylmethyl ether; said ketone compound is selected from the group consisting of 3-hexanone, 2-heptanone, cyclohexanone, and phenylmethylketone; and said ester compound is selected from the group consisting of phenyl acetate and methyl benzoate.

* * * * *